(12) United States Patent
Castro Pineiro et al.

(10) Patent No.: US 7,371,771 B2
(45) Date of Patent: May 13, 2008

(54) ALKENYL-SUBSTITUTED SPIROCYCLIC SULFAMIDES AS INHIBITORS OF GAMMA-SECRETASE

(75) Inventors: Jose Luis Castro Pineiro, Bishops Stortford (GB); Joanne Claire Hannam, Bishops Stortford (GB); Timothy Harrison, Great Dunmow (GB); Andrew Madin, Sawbridgeworth (GB); Mark Peter Ridgill, Watton-at-Stone (GB)

(73) Assignee: Merck Sharp & Dohme Ltd., Hoddesdon, Hertfordshire (GB)

( * ) Notice: Subject to any disclaimer, the term of this patent is extended or adjusted under 35 U.S.C. 154(b) by 559 days.

(21) Appl. No.: 10/511,507

(22) PCT Filed: Apr. 24, 2003

(86) PCT No.: PCT/GB03/01758

§ 371 (c)(1),
(2), (4) Date: Oct. 15, 2004

(87) PCT Pub. No.: WO03/093251

PCT Pub. Date: Nov. 13, 2003

(65) Prior Publication Data

US 2005/0182111 A1    Aug. 18, 2005

(30) Foreign Application Priority Data

May 1, 2002  (GB) ................... 0209991.9

(51) Int. Cl.
*A61K 31/433*   (2006.01)
*A61P 25/28*    (2006.01)
*C07D 498/10*   (2006.01)

(52) U.S. Cl. ..................... 514/372; 548/126
(58) Field of Classification Search ........ 514/372; 548/126
See application file for complete search history.

(56) References Cited

U.S. PATENT DOCUMENTS 3,406,184 A    10/1968    Raasch 3,715,362 A    2/1973    Dominianni
5,703,129 A    12/1997   Felsenstein et al.
2004/0029862 A1  2/2004   Belanger et al.
2004/0049038 A1  3/2004   Collins et al.

FOREIGN PATENT DOCUMENTS

| WO | WO 98/38156 | 9/1998 |
|---|---|---|
| WO | WO 01/70677 | 9/2001 |
| WO | WO 02/36555 | 5/2002 |

OTHER PUBLICATIONS

G. M. Rishton et al., "Fenchylamine Sulfonamide Inhibitors of Amyloid Beta Peptide Production by the Gamma-Secretase Proteolytic Pathway . . . ", J. Med. Chem., 2000, 43, 2297-2299.
J. E. Franz, et al.: Journal of Organic Chemistry, vol. 29, No. 10, Oct. 1964, pp. 2922-2927.
R. Huisgen, et al.: Chemische Berichte, vol. 98, No. 12, Dec. 1965, pp. 3992-4013.
S. Itsuno, et al.: Journal of the Chemical Society, Perkin Transactions 1, No. 10, Jul. 15, 1999 pp. 2011-2016.
M. Narisada, et al.: Journal of Medicinal Chemistry, vol. 31, No. 9, Sep. 1988, pp. 1847-1854.
K. B. Sharpless, et al.: Journal of Organic Chemistry, vol. 41, No. 1, Jan. 9, 1976, pp. 176-177.
Y. Yamaguchi, et al.: Xenobiotica, vol. 26, No. 6, Jun. 1996, pp. 613-626.
L. H. Zalkow, et al.: Journal of the American Chemical Society, vo. 86, No. 19, Oct. 5, 1964.
L. H. Zalkow, et al.: Journal of Organic Chemistry, vol. 28, No. 12, Dec. 1963, pp. 3303-3309.

*Primary Examiner*—Kamal A. Saeed
(74) *Attorney, Agent, or Firm*—William Krouatin; Raynard Yuro

(57) ABSTRACT

Compounds of formula (I) are disclosed: wherein $R^4$ is an alkenyl group of defined structure. The compounds inhibit gamma-secretase, and hence are useful for treatment of Alzheimer's disease.

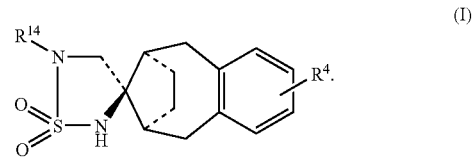

(I)

6 Claims, No Drawings

ALKENYL-SUBSTITUTED SPIROCYCLIC SULFAMIDES AS INHIBITORS OF GAMMA-SECRETASE

CROSS REFERENCE TO RELATED APPLICATIONS

This application is a U.S. National Phase application under 35 U.S.C. § 371 of PCT Application No. PCT/GB03/01758, filed Apr. 24, 2003, which claims priority under 35 U.S.C. § 119 from GB Application No. 0209991.9, filed May 1, 2002.

The present invention relates to a novel class of compounds, their salts, pharmaceutical compositions comprising them, processes for making them and their use in therapy of the human body. In particular, the invention relates to compounds which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although the exact role of the plaques in the onset and progress of AD is not fully understood, it is generally accepted that suppressing or attenuating the secretion of Aβ is a likely means of alleviating or preventing the condition. (See, for example, ID *research alert* 1996 1(2): 1-7; ID *research alert* 1997 2(1):1-8; Current Opinion in CPNS Investigational Drugs 1999 1(3):327-332; and Chemistry in Britain, January 2000, 28-31.)

Aβ is a peptide comprising 39-43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-$APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

There are relatively few reports in the literature of compounds with inhibitory activity towards β- or γ-secretase, as measured in cell-based assays. These are reviewed in the articles referenced above. Many of the relevant compounds are peptides or peptide derivatives.

WO 01/70677 discloses certain sulphonamido-substituted bridged bicycloalkyl derivatives which are useful in the treatment of Alzheimer's disease, but neither discloses nor suggests the compounds of the present invention.

The present invention provides a novel class of non-peptidic compounds which are useful in the treatment or prevention of AD by modulating the processing of APP by the putative γ-secretase, thus arresting the production of Aβ and preventing the formation of insoluble plaques.

According to the invention there is provided a compound of formula I:

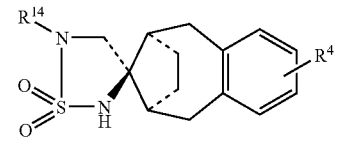

wherein $R^4$ is selected from:

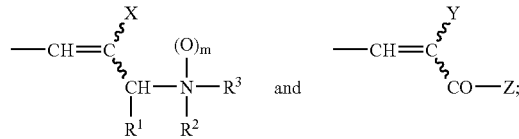

X represents H, halogen, CN or methyl;

$R^1$ represents H or $C_{1-4}$alkyl which is optionally substituted with OH or $C_{1-4}$alkoxy; or $R^1$ and $R^2$ together complete a heterocyclic ring of 3-7 members bearing 0-2 substituents, in addition to $R^3$, selected from halogen, oxo, $NO_2$, CN, $CF_3$, $C_{1-6}$alkyl, $C_{2-6}$acyl, $C_{2-6}$alkenyl, $C_{1-6}$alkoxy, $C_{1-6}$alkoxycarbonyl and Ar;

when $R^1$ represents H or optionally substituted $C_{1-4}$alkyl, $R^2$ and $R^3$ independently represent H, $C_{1-10}$alkyl, $C_{3-10}$cycloalkyl, $C_{3-6}$cycloalkyl$C_{1-6}$alkyl, $C_{2-10}$alkenyl, $C_{2-10}$alkynyl, Ar, heterocyclyl, or heterocyclyl$C_{1-6}$alkyl, wherein the alkyl, cycloalkyl, alkenyl and alkynyl groups optionally bear one substituent selected from halogen, $CF_3$, $NO_2$, CN, Ar, $ArCH_2O$, ArO, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$; and the heterocyclic groups optionally bear up to 3 substituents independently selected from halogen, $NO_2$, CN, $R^{12}$, Ar, $ArCH_2O$, ArO, $ArOCH_2$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

or $R^2$ and $R^3$ together with the nitrogen to which they are mutually attached complete a mono- or bicyclic heterocyclic ring system of 5-10 ring atoms selected from C, N, O and S, said ring system optionally having an additional benzene or heteroaryl ring fused thereto, said heterocyclic system and optional fused ring bearing 0-3 substituents independently selected from halogen, oxo, $NO_2$, CN, $R^{12}$, Ar, $ArCH_2O$, ArO, $ArOCH_2$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

and when $R^1$ completes a ring with $R^2$, $R^3$ represents H, $C_{1-6}$alkyl, $C_{2-6}$acyl, $C_{2-6}$alkenyl or benzyl;

m is 0 or 1, with the proviso that when m is 1 neither $R^2$ nor $R^3$ is H and $R^3$ is not acyl, and that m is 1 when X and $R^1$ are both H;

$R^{11}$ represents H or $R^{12}$;

$R^{12}$ represents $C_{1-6}$alkyl which optionally bears up to 3 halogen substituents or one substituent selected from CN, OH, $C_{1-4}$alkoxy and $C_{1-4}$alkoxycarbonyl;

Y represents halogen, CN or methyl;

Z represents $OR^{11}$ or $N(R^5)R^6$;

$R^5$ and $R^6$ have the same definition as $R^2$ and $R^3$ in the embodiment in which $R^1$ is H or optionally substituted $C^{1-4}$alkyl;

$R^{14}$ represents H or $C_{1-6}$alkyl, $C_{3-7}$cycloalkyl, $C_{3-6}$cycloalkyl$C_{1-6}$alkyl, $C_{2-6}$alkenyl, $C_{2-6}$alkynyl, phenyl or benzyl, any of which optionally bear up to 3 halogen substituents or one substituent selected from CN, $NO_2$, OH, $C_{1-4}$alkoxy, $CO_2H$, $C_{1-4}$alkoxycarbonyl, $C_{2-6}$acyl, $C_{2-6}$acyloxy, mino, $C_{1-4}$alkylamino, di($C_{1-4}$alkyl)amino, $C_{2-6}$acylamino, carbamoyl, $C_{1-4}$alkylcarbamoyl and di($C_{1-4}$alkyl)carbamoyl; and Ar represents phenyl or heteroaryl either of which optionally bears up to 3 substituents independently selected from halogen, $CF_3$, $NO_2$, CN, $OCF_3$, $C_{1-6}$alkyl and $C_{1-6}$alkoxy;

or a pharmaceutically acceptable salt thereof.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, such groups comprise no more than 4 carbon atoms.

The expression "$C_{3-6}$cycloalkyl" as used herein refers to nonaromatic monocyclic or fused bicyclic hydrocarbon ring systems comprising from 3 to 10 ring atoms. Bicyclic systems comprising a nonaromatic hydrocarbon ring of 3-6 members which is fused to a benzene ring are also included. Examples include cyclopropyl, cyclobutyl, cyclopentyl, cyclohexyl, cyclohexenyl, decalinyl, tetralinyl and indanyl.

The expression "$C_{3-6}$ cycloalkyl($C_{1-6}$)alkyl" as used herein includes cyclopropylmethyl, cyclobutylmethyl, cyclopentylmethyl and cyclohexylmethyl.

The expression "$C_{2-6}$acyl" as used herein refers to ($C_{1-5}$alkyl)carbonyl groups, such as acetyl, propanoyl and butanoyl, including cycloalkyl derivatives such as cyclopentanecarbonyl and cyclobutanecarbonyl and halogenated derivatives such as trifluoroacetyl.

The expression "heterocyclyl" as used herein means a cyclic or polycyclic system of up to 10 ring atoms selected from C, N, O and S, wherein at least one ring atom is other than carbon and said atom is part of a non-aromatic ring. Monocyclic systems of up to 6 ring atoms are preferred. Preferably not more than 3 ring atoms are other than carbon. Suitable heterocyclyl groups include azetidinyl, pyrrolidinyl, terahydrofuryl, piperidinyl, piperazinyl, morpholinyl, thiomorpholinyl, tetrahydropyranyl, tetrahydropyridinyl, imidazolinyl, dioxanyl, benzodioxanyl and 5-aza-2-oxabicyclo[2.2.1]heptyl. Unless indicated otherwise, attachment of heterocyclyl groups may be through a carbon or nitrogen atom forming part of the heterocyclic ring. "C-heterocyclyl" indicates bonding through carbon, while "N-heterocyclyl" indicates bonding through nitrogen.

The expression "heteroaryl" as used herein means a cyclic or polycyclic system of up to 10 ring atoms selected from C, N, O and S, wherein at least one of the constituent rings is aromatic and comprises at least one ring atom which is other than carbon. Monocyclic systems comprising 5 or 6 ring atoms are preferred. Preferably not more than 3 ring atoms are other than carbon. Where a heteroaryl ring comprises two or more atoms which are not carbon, not more than one of said atoms may be other than nitrogen. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of suitable heteroaryl ring systems include 1,2,4-triazine and 1,3,5-triazine.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The compounds of formula I exist as two sets of positional isomers, depending on whether $R^4$ is attached at an ortho position relative to the fused ring junction, or at a meta position relative to said junction. Meta attachment is preferred. For each positional isomer, two enantiomeric forms are possible, depending on which of the two available ortho or two available meta positions is occupied. For each positional isomer, the invention extends to both enantiomers, as pure compounds or as enantiomeric mixtures in any proportion. Furthermore, structural formulae depicting one enantiomeric form are to be construed as representing both enantiomeric forms, unless otherwise stated.

The compounds of formula I are alkenyl-substituted benzo-fused bridged bicycloalkane derivatives comprising a spiro-linked cyclic sulphamide moiety. The alkenyl group may exist as either of the possible geometrical isomers, but the isomer in which X or Y is cis with respect to the benzene ring is preferred.

In the compounds of formula I, $R^{14}$ preferably represents optionally substituted $C_{1-6}$alkyl (such as methyl, ethyl, n-propyl, isopropyl, n-butyl, t-butyl, sec-butyl, cyanomethyl, 2-fluoroethyl, methoxyethyl, trifluoromethyl and 2,2,2-trifluoroethyl), $C_{3-7}$cycloalkyl (such as cyclopropyl, cyclobutyl, cyclopentyl and cyclohexyl), $C_{3-6}$cycloalkyl$C_{1-6}$alkyl (such as cyclopropylmethyl, cyclobutylmethyl and cyclopentylmethyl), $C_{2-6}$alkenyl (such as allyl), $C_{2-6}$alkynyl (such as propargyl), or optionally substituted phenyl or benzyl. $R^{14}$ very aptly represents n-propyl or 2,2,2-trifluoroethyl, an in a particular embodiment $R^{14}$ represents 2,2,2-trifluoroethyl.

A subset of the compounds of formula I are in accordance with formula II:

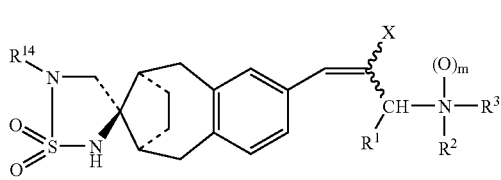

where X, m, $R^1$, $R^2$ and $R^3$ are as previously defined.

X typically represents H, F, CN or methyl.

$R^1$ represents H or optionally substituted $C_{1-4}$alkyl (such as hydroxymethyl), or $R^1$ together with $R^2$ completes a heterocyclic ring as defined previously. When $R^1$ and $R^2$ complete a ring, X is preferably H. Rings completed by $R^1$ and $R^2$ comprise 3-7 atoms, typically 5 or 6 atoms, and suitable examples include pyrrolidine, piperidine, piperazine, tetrahydropyridine, morpholine, thiomorpholine and thiomorpholine-1,1-dioxide. The ring may bear up to two substituents as defined previously, in addition to the $R^3$ group. Preferred substituents include halogen, especially fluorine and chlorine, and $CF_3$. When $R^1$ and $R^2$ complete a ring, $R^3$ represents H, $C_{1-6}$alkyl (such as methyl, ethyl, n-propyl, isopropyl, n-butyl, sec-butyl or t-butyl), $C_{2-6}$acyl (such as acetyl or trifluoroacetyl), $C_{2-6}$alkenyl (such as allyl), or benzyl. In this context, $R^3$ very aptly represents H or benzyl. Specific examples of rings completed by $R^1$ and $R^2$ include 1-benzylpiperidine and 4-trifluoromethylpiperidine.

When $R^1$ is H or optionally substituted $C_{1-4}$alkyl, $R^2$ and $R^3$ independently represent H, $C_{1-10}$alkyl, $C_{3-10}$-cycloalkyl, $C_{3-6}$cycloalkyl$C_{1-6}$alkyl, $C_{2-10}$alkenyl, $C_{2-10}$alkynyl, Ar, heterocyclyl, or heterocyclyl$C_{1-6}$alkyl, wherein the alkyl, cycloalkyl, alkenyl and alkynyl groups optionally bear one substituent selected from halogen, $CF_3$, $NO_2$, CN, Ar, $ArCH_2O$, ArO, $—OR^{11}$, $—SR^{11}$, $—SO_2R^{12}$, $—COR^{11}$, $—CO_2R^{11}$, $—CON(R^{11})_2$, $—OCOR^{12}$, $—N(R^{11})_2$ and $—NR^{11}COR^{12}$; and the heterocyclic groups optionally bear up to 3 substituents independently selected from halogen, $NO_2$, CN, $R^{12}$, Ar, $ArCH_2O$, ArO, $ArOCH_2$, $—OR^{11}$, $—SR^{11}$, $—SO_2R^{12}$, $—COR^{11}$, $—CO_2R^{11}$, $—CON(R^{11})_2$, $—OCOR^{12}$, $—N(R^{11})_2$ and $—NR^{11}COR^{12}$;

or $R^2$ and $R^3$ together with the nitrogen to which they are mutually attached complete a mono- or bicyclic heterocyclic ring system of 5-10 ring atoms selected from C, N, O and S, said ring system optionally having an additional benzene or heteroaryl ring fused thereto, said heterocyclic system and optional fused ring bearing 0-3 substituents independently selected from halogen, oxo, $NO_2$, CN, $R^{12}$, Ar, $ArCH_2O$, ArO, $ArOCH_2$, $—OR^{11}$, $—SR^{11}$, $—SO_2R^{12}$, $—COR^{11}$, $—CO_2R^{11}$, $—CON(R^{11})_2$, $—OCOR^{12}$, $—N(R^{11})_2$ and $—NR^{11}COR^{12}$;

where Ar, $R^{11}$ and $R^{12}$ are as defined previously.

In this context, $R^2$ and $R^3$ typically independently represent H, optionally substituted $C_{1-6}$alkyl (such as methyl, ethyl, 2-methoxyethyl, 2,2,2-trifluoroethyl, 3,3,3-trifluoropropyl, benzyl, furan-2-ylmethyl and pyridin-2-ylmethyl), cycloalkyl (such as cyclopentyl and indanyl), heterocyclyl (such as tetrahydrofuranyl and tetrahydropyranyl) or heterocyclyl$C_{1-6}$alkyl (such as tetrahydropyran-2-ylmethyl, dioxanylmethyl and (4-phenylmorpholin-2-yl)methyl), or $R^2$ and $R^3$ complete a heterocyclic ring system. Suitable ring systems include pyrrolidine, piperidine, tetrahydropyridine, piperazine, morpholine, thiomorpholine, 2,5-diazabicyclo[2,2,1]heptane, 5,6-dihydro-8H-imidazo[1,2-α]pyrazine and spiro[isobenzofuran-1(3H),4'-piperidine]. Preferred ring substituents include halogen, OH, oxo and $R^{12}$ groups (such as methyl, ethyl, propyl, hydroxymethyl, methoxymethyl and trifluoromethyl), acetyl, trifluoroacetyl, methoxycarbonyl, phenoxymethyl, pyridyl and phenyl, wherein the pyridyl and phenyl groups optionally bear up to 2 substituents selected from halogen (especially chlorine or fluorine), $C_{1-6}$alkyl and $C_{1-6}$alkoxy.

When $R^1$ represents H or optionally substituted $C_{1-4}$alkyl, examples of groups represented by $—N(R^2)R^3$ in formula II include N,N-dimethylamino, piperidin-1-yl, morpholin-4-yl, 4-(trifluoroacetyl)piperazin-1-yl, 4-methylpiperazin-1-yl, 4-phenylpiperazin-1-yl,N-(2-methoxyethyl)-N-methylamino, 4-trifluoromethylpiperidin-1-yl, 4,4-difluoropiperidin-1-yl, 5-aza-2-oxabicyclo[2.2.1]hept-5-yl, 1,2,3,6-tetrahydropyridin-1-yl, N-furfurylamino, N-(indan-1-yl)amino, N-(pyridin-2-ylmethyl)amino, N,N-bis(2-methoxyethyl)amino, 3,3-difluoropyrrolidin-1-yl, 4-hydroxy-4-trifluoromethylpiperidin-1-yl, 3-oxopiperazin-1-yl, 3-oxo-4-phenylpiperazin-1-yl, 4-methylpiperidin-1-yl, N-(2,2,2-trifluoroethyl)amino, N-(thiophene-2-ylmethyl)amino, N-methyl-N-(tetrahydrofuran-3-ylmethyl)amino, 2-phenoxymethylmorpholin-4-yl, 3-(pyridin-3-yl)-pyrrolidin-1-yl, N-(4-phenylmorpholin-2-ylmethyl)amino, N-(tetrahydropyran-2-ylmethyl)amino, N-(tetrahydrofuran-3-yl)amino, 3-hydroxypiperidin-1-yl, N-methyl-N-(tetrahydropyran-4-yl)amino, N-(dioxan-2-ylmethyl)amino and N-(tetrahydropyran-4-yl)amino.

In a preferred embodiment, $R^{14}$ is 2,2,2-trifluoroethyl, X is F, CN or methyl, $R^1$ is H and $R^2$ and $R^3$ complete a heterocyclic ring system.

In a particular embodiment, the moiety $—N(R^2)R^3$ represents 4-trifluoromethylpiperidin-1-yl.

Compounds of formula II in which the moiety $—N(R^2)R^3$ represents a tertiary amino group (which optionally may form part of a ring) may be in the form of the corresponding N-oxides (i.e. m=1 in formula I or II). When X and $R^1$ both represent H, the invention is restricted to the aforesaid N-oxides.

Another subset of the compounds of formula I are in accordance with formula III:

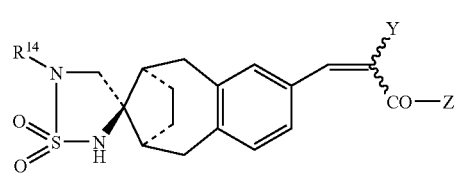

where $R^{14}$, Y and Z are as previously defined.

Y represents halogen (especially F), CN or methyl.

Z typically represents OH, $C_{1-6}$alkoxy (especially methoxy or ethoxy) or $N(R^5)R^6$, where $R^5$ and $R^6$ have the same definition as $R^2$ and $R^3$ when $R^1$ is H or optionally substituted $C^{1-4}$alkyl. Thus, Z may represent any of the groups listed above as possible embodiments of the moiety $—N(R^2)R^3$ in formula II.

In a preferred embodiment, $R^{14}$ is 2,2,2-trifluoroethyl, Y is F, CN or methyl, and Z is as previously defined.

In a particular embodiment, Z represents ethoxy.

Specific compounds in accordance with the invention are disclosed in the Examples appended hereto.

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

The compounds of formulae II and II may be prepared from the triflates of formula IV:

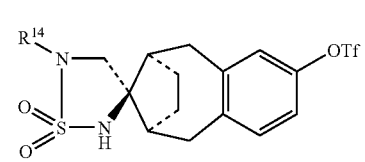

IV where Tf represents trifluoromethanesulphonyl and $R^{14}$ has the same meaning as before.

In one process, the triflate is reacted with carbon monoxide and methanol to provide the methyl carboxylate V:

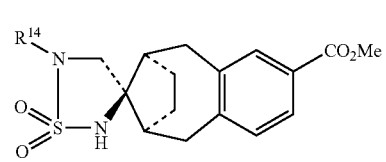

V where $R^{14}$ has the same meaning as before. The reaction takes place in DMSO at 80° C. in the presence of triethylamine, bis(diphenylphosphino)propane and Pd(II) acetate.

Reduction of the ester V to the corresponding benzyl alcohol, followed by oxidation to the corresponding aldehyde, then condensation with $(EtO)_2PO—CHX—CO_2Et$ provides the alkenyl esters VI:

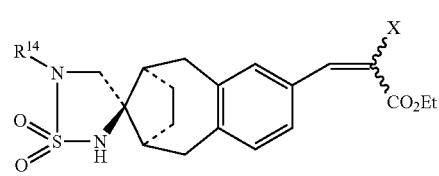

VI where X and $R^{14}$ have the same meanings as before. The reduction may be effected by treatment with diisobutylaluminium hydride in THF at −78° C., the subsequent oxidation by treatment with pyridinium dichromate in dichloromethane, and the condensation takes place in THF at ambient temperature in the presence of a base such as LiOH.

The compounds of formula VI in which X is other than H correspond to compounds of formula III in which Z represents ethoxy. Alkaline hydrolysis of these compounds provides the compounds of formula III in which Z is OH, which may be coupled with $R^{12}OH$ or $R^5R^6NH$ where $R^{12}$, $R^5$ and $R^6$ have the same meanings as before to provide the remaining compounds of formula III. Standard techniques of ester- or amide-formation may be used for this purpose.

The alkenyl esters VI may be reduced to the corresponding allyl alcohols VII(a), which may be reacted with $PBr_3$ to provide the allyl bromides VII(b), which in turn undergo nucleophilic displacement with $R^2R^3NH$ to provide the amines VII(c):

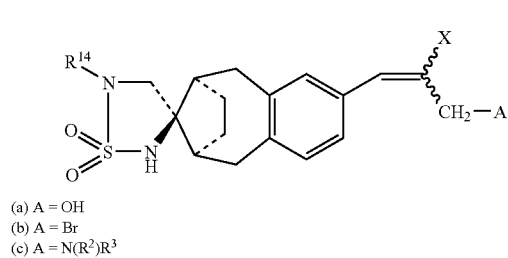

(a) A = OH
(b) A = Br
(c) A = N($R^2$)$R^3$ where X, $R^1$, $R^2$ and $R^3$ have the same meanings as before. The reduction of VI may be effected by treatment with diisobutylaluminium hydride in THF at −10° C., the subsequent reaction with PBr$_3$ takes place in dichloromethane at −30° C., and the nucleophilic displacement is typically carried out at ambient temperature in dichloromethane in the presence of a tertiary amine such as diisopropylethylamine.

Alternatively, the aldehydes obtained by sequential reduction and oxidation of esters V may be reacted with acrylonitrile to provide allylic alcohols VA:

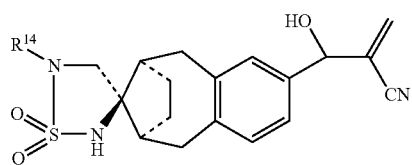

where $R^{14}$ has the same meaning as before. The reaction takes place in aqueous dioxan in a sealed tube at ambient temperature in the presence of 1,4-diazabicyclo[2,2,2]octane. Subsequent treatment with PBr$_3$ and nucleophilic displacement as described above provides an alternative route to compounds of formula VII(c) in which X is CN.

The compounds of formula VII(c) correspond to compounds of formula II in which $R^1$ is H and m is 0.

In another process, a triflate IV is reacted with an alkyne HC≡C—CH$_2$—$R^{1a}$ to provide a compound of formula VIII:

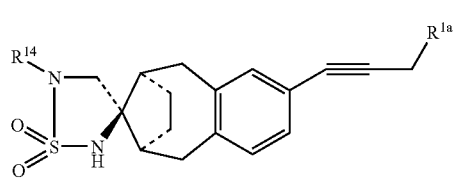

where $R^{1a}$ represents H or C$_{1-4}$alkyl which is optionally substituted with OH or C$_{1-4}$alkoxy, and $R^{14}$ has the same meaning as before. The reaction takes place in the presence of (Ph$_3$P)$_4$Pd(0), Ph$_3$P, copper iodide and triethylamine in dioxan at 100° C.

Treatment of alkynes VIII with $R^2R^3$NH provides the compounds of formula IX:

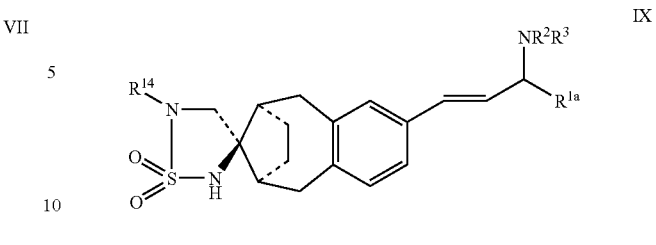

where $R^{14}$, $R^{1a}$, $R^2$ and $R^3$ have the same meanings as before. The reaction takes place in refluxing dioxan in the presence of (Ph$_3$P)$_4$Pd(0) and benzoic acid. The compounds of formula IX correspond to the compounds of formula II in which X is H, m is 0 and $R^1$ is C$_{1-4}$alkyl which is optionally substituted with OH or C$_{1-4}$alkoxy.

In another process, a triflate IV is reacted with an alkyne HC≡C—CH$_2$(CH$_2$)$_n$NR$^{3a}$ to provide compounds of formula X:

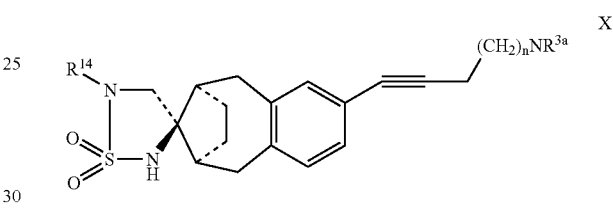

where n is 3 or 4, $R^{3a}$ represents H, C$_{1-6}$alkyl, C$_{2-6}$alkenyl or benzyl and $R^{14}$ has the same meaning as before. The reaction takes place under similar conditions to the conversion of IV to VIII.

Cyclisation of the compounds of formula X under similar conditions to the preparation of compounds IX provides compounds XI:

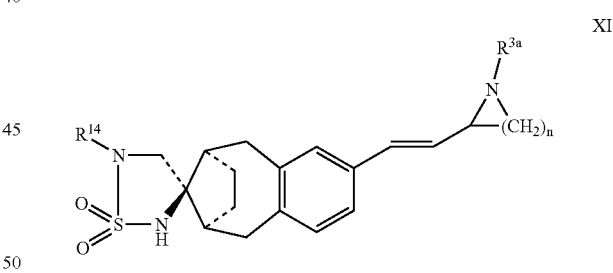

where n, $R^{14}$ and $R^{3a}$ have the same meanings as before. Such compounds correspond to compounds of formula II in which X is H, $R^1$ and $R^2$ complete a pyrrolidine or piperidine ring and $R^3$ represents H, C$_{1-6}$alkyl, C$_{2-6}$alkenyl or benzyl.

In another process, the triflates IV are converted to boronic acid derivatives XII:

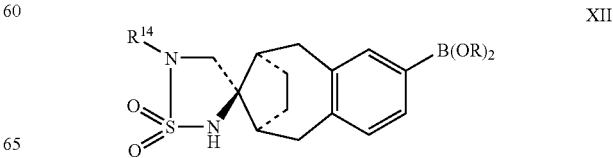

where R represents H or alkyl, or the two OR groups complete a cyclic boronate ester such as the pinacolate. The conversion may be achieved by conventional means using a suitable boron reagent, such as bis(pinacolato)diboron, in the presence of a Pd(II) catalyst such as bis(diphenylphosphinoferrocene)dichloropalladium(II), typically in the presence of potassium acetate in DMF at 100° C.

Coupling of the boron compounds XII with an iodoalkene I—CH=CH—CHR$^1$—N(R$^2$)Boc provides compounds of formula XIII(a):

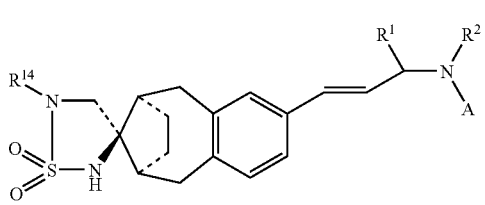

XIII (a) A = Boc
(b) A = H where R$^1$ and R$^2$ complete a heterocyclic ring, Boc represents t-butoxycarbonyl and R$^{14}$ has the same meaning as before. The coupling may be carried out in THF at 60° C. in a sealed tube in the presence of tris(dibenzylideneacetone)dipalladium(0), tributylphosphine and caesium carbonate.

Treatment of the compounds XIII(a) with acid provides the deprotected compounds XIII(b), which are compounds in accordance with formula II in which m is 0, X is H, R$^1$ and R$^2$ complete a ring and R$^3$ is H.

Individual compounds in accordance with formula I may be converted to different compounds in accordance with formula I by application of known synthetic techniques. Alternatively, such transformations may be carried out on the precursors of the compounds of formula I. For example, compounds in which the moiety —N(R$^2$)R$^3$ represents a tertiary amino group may be converted to the corresponding N-oxides (m=1) by conventional oxidative techniques, e.g. treatment with m-chloroperoxybenzoic acid at ambient temperature in an inert solvent such as dichloromethane.

Where they are not commercially available, the above-mentioned reagents may be prepared by conventional routes. The synthesis of triflate IV in which R$^{14}$ represents 2,2,2-trifluoroethyl is described in the Examples, and analogous routes may be followed for other identities of R$^{14}$.

Where more than one isomer can be obtained from the above-described reaction schemes, then the resulting mixture of isomers can be separated by conventional means.

Where the above-described processes for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50-70% confluency in the presence of sterile 10 mM sodium butyrate.

(2) Cells are placed in 96-well plates at 30,000/well/100 μL in minimal essential medium (ME) (phenol red-free)+ 10% foetal bovine serum (FBS), 50 mM HEPES buffer (pH7.3), 1% glutamine, 0.2 mg/ml G418 antibiotic, 10 mM sodium butyrate.

(3) Make dilutions of the compound plate. Dilute stock solution to 5.5% DMSO/110 μM compound. Mix compounds vigorously and store at 4° C. until use.

(4) Add 10 μL compound/well. M plate briefly, and leave for 18 h in 37° C. incubator.

(5) Remove 90 μL of culture supernatant and dilute 1:1 with ice-cold 25 mM HEPES (pH0.3), 0.1% BSA, 1.0 mM EDTA (+broad spectrum protease inhibitor cocktail; pre-aliquotted into a 96-well plate). Mix and keep on ice or freeze at −80° C.

(6) Add back 100 μL of warm MEM+10% FBS, 50 mM HEPES (pH7.3), 1% glutamine, 0.2 mg/ml G418, 10 mM sodium butyrate to each well, and return plate to 37° C. incubator.

(7) Prepare reagents necessary to determine amyloid peptide levels, for example by ELISA assay.

(8) To determine if compounds are cytotoxic, cell viability following compound administration is assessed by the use of redox dye reduction. A typical example is a combination of redox dye MTS (Promega) and the electron coupling reagent PES. This mixture is made up according to the manufacturer's instructions and left at room temperature.

(9) Quantitate amyloid beta 40 and 42 peptides using an appropriate volume of diluted culture medium by standard ELISA techniques.

(10) Add 15 μL/well MTS/PES solution to the cells; mix and leave at 37° C.

(11) Read plate when the absorbance values are approximately 1.0 (mix briefly before reading to disperse the reduced formazan product).

Alternative assays are described in *Biochemistry*, 2000, 39(30), 8698-8704.

The Examples of the present invention all had an ED$_{50}$ of less than 100 nM, typically less than 50 nM and in most cases less than 10 nM in at least one of the above assays.

The following examples illustrate the present invention.

EXAMPLES

Intermediate 1

Step 1

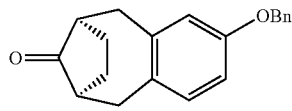

A mixture of 2-hydroxy-5,6,7,8,9,10-hexahydro-6,9-methanobenzo[α][8]annulen-11-one (15 g; J. Org. Chem 1982, 47, 4329), K$_2$CO$_3$ (20.5 g) and benzyl bromide (10.6 ml) in DMF (100 ml) was stirred for 48 hrs at room temperature. The reaction was diluted with water (500 ml) and extracted with EtOAc (3×150 ml). The combined organic phases were washed with water (2×300 ml), brine (150 ml), dried and concentrated to give a gummy oil which crystallized on standing and after trituration with ether the title benzyl ether (19.5 g, 90%) as a white solid (360 MHz $^1$H, δ-CDCl$_3$) 1.32 (2H, m), 1.85 (2H, m), 2.57 (2H, m), 2.87 (4H, m), 5.05 (2H, s), 6.82 (2H, m), 7.11 (1H, d, J=8.2), 7.37 (5H, m).

Step 2

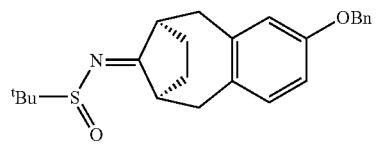

A solution of the product from Step 1 (20 g, 68 mmol), (+/−)tert-butyl sulfinamide (9.2 g, 76 mmol) and titanium (IV) ethoxide (tech., 29.2 mL, 140 mmol) in dry THF (140 mL) was stirred and heated at reflux under nitrogen for 4 hours. The reaction was allowed to cool to room temperature and poured into rapidly stirred brine (160 mL). The mixture was stirred for 20 minutes, then filtered through Hyflo®, washing with ethyl acetate. The filtrate was transferred to a separating funnel. The layers were separated, and the aqueous layer was extracted with ethyl acetate (×1). The combined organic extracts were washed with brine, then dried (Na$_2$SO$_4$), filtered and evaporated. The residue was purified by chromatography on silica, eluting with 20→30% ethyl acetate/hexanes, to give the imine (24.9 g, 93%) as a colourless solid. MS(ES+) 396, MH$^+$.

Step 3

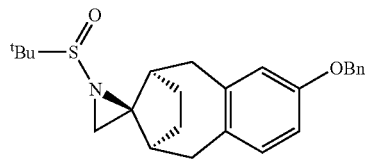

Sodium hydride (60% dispersion in oil, 3.8 g, 95 mmol) was added portionwise to a stirred suspension of trimethyl sulfoxonium iodide (21 g, 95 mmol) in dry DMSO (150 mL) at room temperature under nitrogen. After 90 minutes at room temperature, a solution of the product from Step 2 (24.9 g, 95 mmol) in dry DMSO (250 mL) was added such that the internal temperature remained below 30° C. The mixture was stirred at room temperature for 4 hours, then quenched with water (1 L). The precipitate was collected by filtration. The solid was taken up in dichloromethane and washed with brine. The organic layer was dried (Na$_2$SO$_4$), filtered and evaporated. The residue was purified by chromatography on silica, eluting with 5→10% ethyl acetate/dichloromethane, to give the aziridine (23.2 g, 90%) as a colourless solid. MS(ES+) 410, MH$^+$.

Step 4

Trifluoroethyl amine (70 mL, 880 mmol) was added to a stirred suspension of the product from Step 3 (68.4 g, 167 mmol) and anhydrous zinc iodide (54 g, 170 mmol) in dry 1,2-dichloroethane (300 mL) at room temperature under nitrogen. The resulting solution was heated at 75° C., protected from light for 24 hours, an additional portion of trifluoroethyl amine (70 mL, 880 mmol) added and the reaction maintained at 75° C. for a further 16 hours. The reaction was allowed to cool, then diluted with dichloromethane (500 mL) and water (400 mL). Sufficient sodium carbonate was then added to adjust the aqueous layer to ~pH 11. The small amount of precipitate was removed by filtration through Hyflo®. The layers were separated and the aqueous layer was extracted with dichloromethane (×3). The combined organic extracts were dried (Na$_2$SO$_4$), filtered and evaporated. The residue was purified by chromatography on silica, eluting with 5→10% ethyl acetate/dichloromethane, then with 10→20% methanol/dichloromethane, to give the diamine (59.6 g, 88%) as a thick oil. MS(ES+) 405, MH$^+$.

Step 5

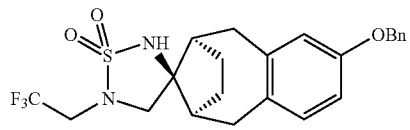

A solution of the product from Step 4 (59.6 g, 147 mmol) and sulfamide (42.5 g, 442 mmol) in dry pyridine (350 mL) was stirred and heated at reflux under nitrogen for 4 hours. The reaction was allowed to cool, then the pyridine was removed in vacuo. The residue was azeotroped with toluene (×2) and the residue partitioned between dichloromethane (400 mL) and 1N hydrochloric acid (400 mL). The layers were separated and the aqueous layer was extracted with dichloromethane (3). The combined organic extracts were dried (Na$_2$SO$_4$), filtered and evaporated. The residue was purified by chromatography on silica, eluting with dichloromethane, then 1→2→4% ethyl acetate/dichloromethane to give the cyclic sulfamide (53 g, 80%) as a colourless solid. $^1$H NMR (360 MHz, CDCl$_3$) δ$_H$ 1.34 (2H, m), 1.70 (2H, m), 2.41 (2H, m), 2.62 (2H, m), 3.11 (2H, d, J=15.9), 3.20 (1H, d, J=15.9), 3.42 (2H, ABq, J=9.3, 13.3), 3.67 (2H, dq, J=2.2, 8.7), 4.76 (1H, s), 5.02 (2H, s), 6.72 (2H, m), 6.99 (1H, d, J=7.8), 7.37 (5H, m).

Step 6

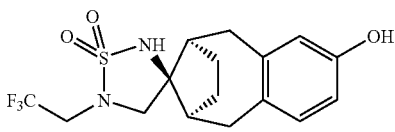

A solution of the product from Step 5 (3.9 g, 8.4 mmol) in methanol/ethyl acetate (4:1, 150 mL) was hydrogenated at 35 psi over 10% palladium on carbon (500 mg) for 4 hours at room temperature. The catalyst was removed by filtration through Hyfloo. The filtrate was evaporated, and the residue was purified by filtration through a pad of silica, eluting with 50% ethyl acetate/dichloromethane to give the phenol (3.2 g) colourless solid. $^1$H NMR(360 MHz, d$_6$-DMSO) δ$_H$ 1.06 (2H, m), 1.65 (2H, m), 2.29 (2H, m), 2.42 (2H, m), 3.04 (1H, d, J=15.6), 3.11 (1H, d, J=15.6), 3.43 (2H, s), 3.99 (2H, brq, J=9.6), 6.47 (2H, m), 6.85 (1H, d, J=8) 7.93 (1H, s), 9.02 (1H, s).

Step 7

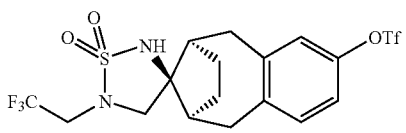

Pyridine (2.1 mL, 26 mmol) was added dropwise to a stirred solution/suspension of the product from Step 6 (7.7 g, 20 mmol) and triflic anhydride (4.3 mL, 25.6 mmol) in dry dichloromethane (200 mL) at 0° C. under nitrogen. The cooling bath was removed and the reaction was stirred at room temperature for 4 hours. Water (300 mL) was added and the layers were separated. The aqueous layer was extracted with dichloromethane (×2). The combined extracts were washed with brine (×1), then dried (Na$_2$SO$_4$), filtered and evaporated. The residue was purified by chromatography on silica, eluting with 5% ethyl acetate/dichloromethane, to give the triflate (6.7 g, 65%) as an off white solid. $^1$H NMR (360 MHz, d$_6$-DMSO) δ$_H$ 0.99 (2H, m), 1.71 (2H, m), 2.38 (2H, brm), 2.69 (2H, m), 3.16 (1H, d, J=15.7), 3.18 (1H, d, J=15.7), 3.46 (2H, s), 4.02 (2H, brq, J=9.6), 7.18-7.31 (3H, m), 8.04 (1H, s).

Example 1

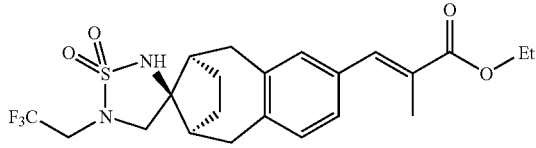

Step 1

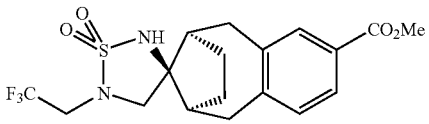

A solution of Intermediate 1 (6.7 g, 13 mmol), 1,3-bis(diphenylphosphino)propane (540 mg, 1.3 mmol) and triethylamine (25 mL, 180 mmol) in dry DMSO (180 mL) and methanol (120 mL) was deoxygenated by bubbling carbon monoxide through the solution for 15 minutes. Palladium (II) acetate (300 mg, 1.3 mmol) was added and deoxygenation was continued for a further 5 minutes. The reaction then heated at 80° C. for 4 hours, with a slow stream of carbon monoxide bubbling though the solution. The reaction was allowed to cool, then diluted with water (1 L) and the mixture extracted with ethyl acetate (×3). The combined extracts were washed with brine (×1), then dried (Na$_2$SO$_4$), filtered and evaporated. The residue was purified by chromatography on silica, eluting with 100% dichloromethane to 5% ethyl acetate/dichloromethane, to give the ester (4.8 g, 88%) as a pale yellow solid. $^1$H NMR (360 MHz, CDCl$_3$) δ$_H$ 1.28 (2H, m), 1.72 (2H, m), 2.48 (2H, brm), 2.78 (2H, m), 3.23 (1H, d, J=15.4), 3.27 (1H, d, J=15.4), 3.43 (2H, ABq, J=9.5, 11.1), 3.68 (2H, q, J=8.7), 3.90 (3H, s), 4.79 (1H, s), 7.17 (1H, d, J=8.3), 7.78 (2H, m).

Step 2

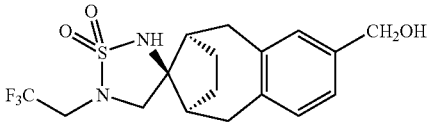

Dibal-H (1M in PhMe, 49 mL, 49 mmol) was added slowly to a stirred solution of the product from Step 1 (5.1 g, 12.2 mmol) in dry THF (100 mL) at −78° C. under nitrogen. After 30 minutes the reaction was allowed to warm to −10° C. and maintained at this temperature for 3 hours. The reaction was quenched with methanol and allowed to warm to room temperature. 1N hydrochloric acid (100 mL) was added slowly and the mixture extracted with ethyl acetate (×3). The combined extracts were washed with brine (×1), then dried (Na$_2$SO$_4$), filtered and evaporated to give a dark foam (5.2 g) which was used without further purification. $^1$H NMR (360 MHz, CDCl$_3$) δ$_H$ 1.35 (2H, m), 1.71 (2H, m), 2.43 (2H, brm), 2.68 (1H, d, J=16.1), 2.70 (1H, d, J=16.1), 3.17 (1H, d, J=15.9), 3.20 (1H, d, J=15.9), 3.43 (2H, s), 3.69 (2H, q, J=8.7), 4.65 (2H, brs), 4.73 (1H, s), 7.10 (3H, m).

Step 3

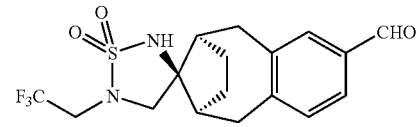

Pyridinium dichromate (6.9 g, 18 mmol) was added to a stirred solution of the product from Step 2 (5.2 g) in dry dichloromethane (120 mL) at room temperature. The mixture was stirred at this temperature overnight, then loaded directly on to a pad of silica. The pad was eluted with dichloromethane, then 20% ethyl acetate/dichloromethane to give the aldehyde (4.2 g, 89%) as a pale yellow solid. $^1$H NMR (360 MHz, CDCl$_3$) $\delta_H$ 1.27 (2H, m), 1.74 (2H, m), 2.50 (2H, brm), 2.82 (2H, m), 3.26 (1H, d, J=13.9), 3.30 (1H, d, J=13.9), 3.45 (2H, Abq, J=9.4, 11.5), 3.69 (2H, q, J=8.7), 4.79 (2H, s), 7.28 (1H, d, J=7.6), 7.64 (2H, m), 9.96 (1H, s).

Step 4

To a solution of aldehyde (0.194 g) from Step 3 and triethyl 2-phosphonopropionate (0.357 g) in THF (4 ml) at room temperature was added LiOH (36 mg) in one portion and the mixture stirred o/n. Added 1M HCl and extracted with EtOAc (3×), then washed the combined organic extracts with brine, dried and concentrated. The crude product was purified by chromatography on silica eluting with 15% EtOAc/hexane to give the desired product as a white solid (0.220 g, 93%). $^1$H NMR (360 MHz, CDCl$_3$) $\delta_H$ 1.35 (3H, t, J=7.1), 1.55 (2H, m), 1.73 (2H, m), 2.11 (3H, d, J=1.3), 2.46 (2H, m), 2.71 (2H, m), 3.23 (2H, dd, J=16.0, 5.3), 3.44 (2H, s), 3.68 (2H, q, J=8.7), 4.26 (2H, q, J=7.1), 4.71 (1H, s), 7.12 (2H, m), 7.19 (1H, m), 7.62 (1H, m).

Example 2

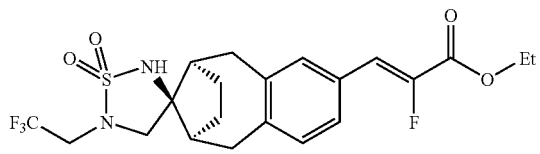

Triethylamine (0.08 ml) was added to a mixture of the aldehyde from Example 1, Step 3 (0.150 g), triethyl 2-fluoro-2-phosphonoacetate (0.131 g) and magnesium bromide (0.121 g) in THF (20 ml) at 0° C. under nitrogen. The reaction was stirred for 2 hours at 0° C. Added 2N HCl (40 ml) and extracted with EtOAc (3×50 ml). The combined organic phases were washed with brine (50 ml). Drying, concentration and column chromatography on silica eluting with 20% EtOAc/hexane gave the unsaturated ester (0.121 g, 66%). $^1$H NMR (400 MHz, CDCl$_3$) $\delta_H$ 1.27 (2H, m), 1.38 (3H, t, J=7.1), 1.72 (2H, m), 2.47 (2H, m), 2.73 (2H, m), 3.23 (2H, m), 3.44 (2H, s), 3.68 (2H, q, J=8.7), 4.34 (2H, q, J=7.1), 4.74(1H, s), 6.8 (1H, d, J=35.4), 7.14 (1H, m), 7.40 (2H, m).

Example 3

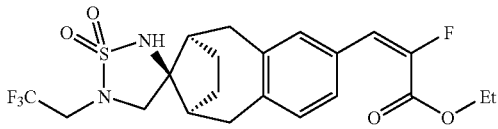

Prepared by the procedure of Example 1 using triethyl 2-fluoro-2-phosphonoacetate instead of triethyl 2-phosphonopropionate. $^1$H NMR (400 MHz, CDCl$_3$) $\delta_H$ 1.27 (3H, t, J=7.1), 1.33 (2H, m), 1.72 (2H, m), 2.45 (2H, m), 2.77 (2H, m), 3.20 (2H, dd, J=16.0, 3.4), 3.43 (2H, s), 3.68 (2H, q, J=8.7), 4.26 (2H, dq, J=1.6, 7.1), 4.67 (1H, s), 6.83 (1H, d, J=23.0), 7.08 (1H, m), 7.27 (2H, m).

Example 4

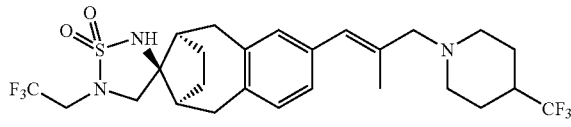

Step 1.

To a solution of the product (0.204 g) from Example 1 in THF (10 ml) at –10° C. under nitrogen was added 1M DIBAL in toluene (1.73 ml) dropwise. Stirred for 5 hrs, at –10° C. to 0° C., added methanol (few drops) and stirred for 5 mins. Added 1M HCl, allowed to warm to room temperature, extracted with EtOAc (3×) and washed with brine. The combined organic extracts were dried (MgSO$_4$), filtered and evaporated. The residue was purified by chromatography on silica gel eluting with 30% EtOAc/hexane to give the allylic alcohol (0.177 g, 95%).

Step 2.

A solution of the alcohol from Step 1 (60 mg) in dry DCM (3 ml) was cooled to –30° C. Added PBr$_3$ (0.07 ml, 1.0M in DCM) dropwise and allowed to warm to 0° C. over 1 hr. Added saturated sodium bicarbonate solution and filtered through celite, washing with DCM. The layers were separated and the organics dried (MgSO$_4$), filtered and evaporated. The crude allylic bromide was dissolved in DCM (2 ml) then 4-trifluoromethylpiperidine (85 mg) and DIPEA (90 mg) were added and the reaction was stirred for 16 hours at rt. Added water (10 ml) and extracted with DCM (3×10 ml), the combined organic phases were washed with brine (20 ml), dried (MgSO$_4$), filtered and evaporated. The residue was purified by chromatography on silica gel eluting with 15% EtOAc/hexane then dissolved in Et$_2$O/MeOH, cooled to 0° C. and bubbled in HCl for 5 mins. Concentrated and triturated with Et$_2$O to give the desired compound (HCl salt) as a white powder (55 mg, 65%). $^1$H NMR (360 MHz, MeOH) $\delta_H$ 1.19 (2H, m), 1.76 (2H, m), 1.95 (2H, m), 2.06 (3H, s), 2.21 (2H, m), 2.45 (2H, m), 2.65 (3H, m), 3.06 (2H, m), 3.31 (2H, m), 3.50 (2H, s), 3.68 (2H, m), 3.85 (4H, m), 6.74 (1H, s), 7.13 (3H, m). MS(ES+) 566, MH$^+$.

Example 5

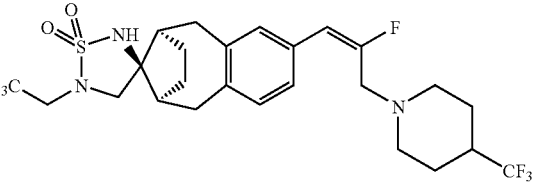

Prepared from the product of Example 3 by the method of Example 4. $^1$H NMR (360 MHz, MeOH) $\delta_H$ 1.19 (2H, m), 1.77 (2H, m), 1.86 (2H, m), 2.16 (2H, m), 2.46 (2H, m), 2.67 (3H, m), 3.08 (2H, m), 3.31 (2H, m), 3.50 (2H, s), 3.64 (2H, m), 3.86 (2H, q, J=9.1), 4.24 (2H, m), 6.88 (1H, d, J=21.4), 7.05 (2H, m), 7.18 (1H, m). MS(ES+) 570, MH$^+$.

Example 6

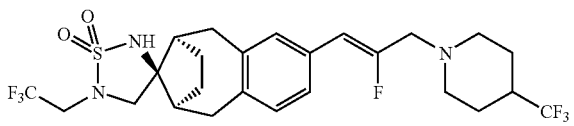

Prepared from the product of Example 2 by the method of Example 4. $^1$H NMR (360 MHz, MeOH) $\delta_H$ 1.18 (2H, m), 1.76 (2H, m), 1.88 (2H, m), 2.22 (2H, m), 2.46 (2H, m), 2.64 (3H, m), 3.15 (2H, m), 3.31 (2H, m), 3.50 (2H, s), 3.71 (2H, m), 3.86 (2H, q, J=9.1), 4.15 (2H, m), 6.19 (1H, d, J=38.8), 7.14 (1H, m), 7.34 (2H, m). MS(ES+) 570, MH$^+$.

Example 7

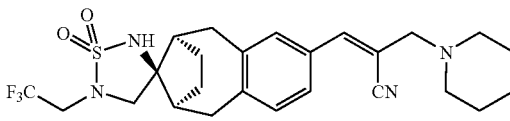

Step 1

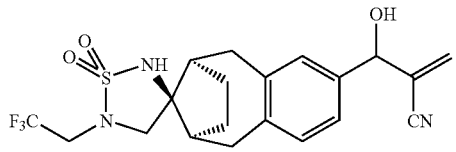

A solution of aldehyde (660 mg, 1.7 mmol) from Example 1, Step 3, acrylonitrile (340 μL, 5.2 mmol) and 1,4-diazabicyclo[2.2.2]octane (190 mg, 1.7 mmol) in dioxane/water (1:1, 18 mL) was stirred at room temperature under nitrogen in a sealed tube for 10 days. The dioxane was removed in vacuo and the aqueous layer was extracted with dichloromethane (×4). The combined extracts were dried (Na$_2$SO$_4$), filtered and evaporated. The residue was purified by chromatography on silica, eluting with 5→10→20% ethyl acetate/dichloromethane, to give the alcohol (674 mg, 90%) as a colourless foam: $^1$H NMR (400 MHz, CDCl$_3$) $\delta_H$ 1.67-1.72 (2H, m), 2.42-2.45 (2H, m), 2.69 (2H, dd, J=16.0, 7.7), 3.15-3.21 (2H, m), 3.42 (2H, s), 3.68 (2H, q, J=8.7), 4.88 (1H, br s), 5.27 (1H, s), 6.05 (1H, m), 6.13-6.15 (1H, m), 7.11-7.16 (3H, m).

Step 2

Phosphorus tribromide (1.0 M in dichloromethane, 115 μL, 0.115 mmol) was added to a solution of the alcohol from Step 1 (100 mg, 0.23 mmol) in dry dichloromethane (2 mL) at 0° C. under nitrogen. The reaction was stirred at 0° C. for 30 minutes, then at room temperature for 1 hour. The reaction was recooled in an ice bath, then quenched with saturated aqueous sodium hydrogen carbonate (2 mL). The mixture was partitioned between dichloromethane and water, the layers separated and the aqueous layer extracted with dichloromethane (×2). The combined extracts were washed with brine (×1), dried (Na$_2$SO$_4$), filtered and evaporated to give the allylic bromide. This was used without further purification.

The bromide was taken up in dry dichloromethane (1 mL) at room temperature under nitrogen. Diisopropylethylamine (200 μL, 1.15 mmol) and 4-trifluoromethylpiperidine (150 mg, 1.0 mmol) were added. The solution was stirred at room temperature overnight, then partitioned between dichloromethane and saturated aqueous sodium hydrogen carbonate. The aqueous layer was extracted with dichloromethane (×2), and the combined extracts washed with brine (×1), dried (Na$_2$SO$_4$), filtered and evaporated. The residue was purified by chromatography on silica, eluting with 2→4→6→8% ethyl acetate/dichloromethane, to give the amine (55 mg, 41%) as a colourless solid: $^1$H NMR (360 MHz, CDCl$_3$) $\delta_H$ 1.29-1.34 (2H, m), 1.67-1.76 (4H, m), 1.84-1.88 (2H, m), 1.98-2.12 (3H, m), 2.22-2.50 (2H, m), 2.74 (2H, dd, J=16.1, 7.7), 3.01-3.06 (2H, m), 3.20-3.27 (4H, m), 3.43 (2H, s), 3.68 (2H, q, J=8.7), 4.69 (1H, s), 7.02 (1H, s), 7.16 (1H, d, J=7.9), 7.49 (1H, s), 7.59 (1H, d, J=7.9). MS(ES+) 577, MH$^+$.

Example 8

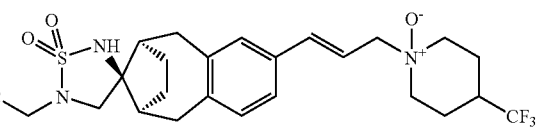

Step 1

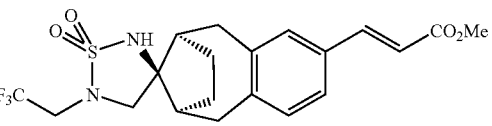

Prepared by the procedure of Example 1 Step 4 by condensation of the aldehyde of Example 1 Step 3 with methyl diethyl phosphonoacetate. $^1$H NMR (360 MHz, CDCl$_3$) $\delta_H$ 1.30 (2H, m), 1.73 (2H, m), 2.46 (2H, brm), 2.72 (2H, m), 3.23 (2H, d, J=15.9), 3.44 (2H, s), 3.68 (2H, q, J=8.7), 3.80 (3H, s), 4.65 (2H, brs), 4.80 (1H, s), 6.40 (1H, d, J=16), 7.11 (1H, d, J=7.7), 7.27 (2H, m), 7.66 (1H, d, J=16).

Step 2

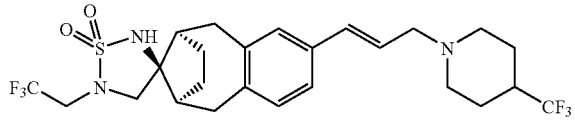

Prepared from the product of Step 1 using the procedure of Example 4. The enantiomers were separated by chiral hplc (chiralcel OD, 25% (25 MM IBU—NH$_2$ in MEOH)/ CO$_2$ 100 bar, 35° C.). The first eluted enantiomer was dissolved in Et$_2$O/MeOH, cooled to 0° C. and bubbled in HCl for 5 mins. Concentrated and triturated with Et$_2$O to give the desired compound. $^1$H NMR (400 MHz, DMSO) $\delta_H$ 1.09 (2H, m), 1.45 (2H, dq, J=3.6, 12.4), 1.68 (2H, m), 1.77 (2H, m), 1.95 (2H, m), 2.26 (1H, m), 2.35 (2H, m), 2.56 (2H, m), 2.95 (2H, m), 3.15 (4H, m), 3.45 (2H, s), 4.01 (2H, q, J=9.6), 6.22 (1H, dt, J=15.9, 6.6), 6.45 (1H, d, J=15.9), 7.04 (1H, m), 7.16 (2H, m), 7.99 (1H, s). MS(ES+) 552, MH$^+$.

Step 3

A mixture of the allylic amine from Step 2 (21 mg) and mCPBA (9 mg) in DCM (2 ml) was stirred at rt for 20 minutes. Saturated sodium bicarbonate solution was added and the reaction was extracted with DCM (×3). The combined organic extracts were dried (MgSO₄), filtered and evaporated. The residue was purified by chromatography on silica gel eluting with 5% MeOH/DCM to give the title compound (10 mg, 45%). ¹H NMR (360 MHz, MeOH) $\delta_H$ 1.19 (2H, m), 1.74 (2H, m), 1.86 (2H, m), 2.28-2.44 (6H, m), 2.64 (2H, m), 3.31 (5H, m), 3.49 (2H, s), 3.85 (2H, q, J=9.2), 4.04 (2H, d, J=7.4), 6.49 (1H, dt, J=15.7, 7.4), 6.79 (1H, d, J=15.7), 7.08 (1H, d, J=7.6), 7.24 (2H, m). MS(ES+) 568, MH⁺.

Example 9

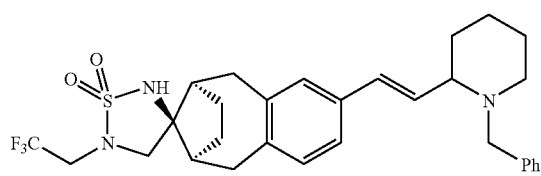

Step 1

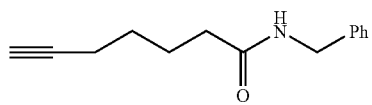

1-(3-dimethylaminopropyl)-3-ethylcarbodiimide (3.3 g, 17.4 mmol) was added to a mixture of 6-heptynoic acid (1.1 g, 8.7 mmol), benzylamine (950 µl, 8.7 mmol), 1-hydroxybenzotriazole (1.2 g, 8.7 mmol) and triethylamine (2.4 ml, 17.4 mmol) in tetrahydrofuran (25 ml) and the mixture was stirred at room temperature for 16 hours. The reaction was diluted with sodium hydrogen carbonate (sat, 60 ml) and extracted with ethyl acetate (2×100 ml). The extracts were washed with brine, dried (MgSO₄) and evaporated in vacuo to a brown solid (2.1 g, 99%). (ES+) 216 ([MH]⁺).

Step 2

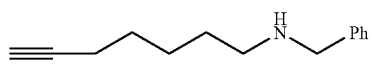

Lithium aluminium hydride (1 m in THF, 10 ml, 10 mmol) was added to a solution of the amide (Step 1) (1.0 g, 4.6 mmol) in THF (20 ml) and the mixture was heated at reflux for 16 hours. The reaction was cooled in ice and treated successively with water (0.4 ml), sodium hydroxide (0.4 ml) and water (1.2 ml) allowing 10 minutes between additions. The mixture was filtered through a bed of celite® and washed through with THF. The filtrate was evaporated in vacuo to a yellow oil (924 mg, 99%). (ES+) 202 ([MH]⁺).

Step 3

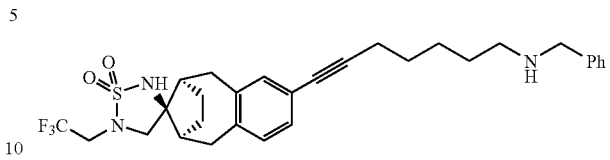

A mixture of Intermediate 1 (300 mg, 0.6 mmol), alkyne from Step 2 (482 mg, 2.4 mmol), tetrakis-triphenylphospine palladium(0) (35 mg, 5 mol %), triphenylphosphine (16 mg, 10 mol %) and copper iodide (12 mg, 10 mol %) in triethylamine (5 ml) in a sealed tube, was purged with nitrogen and then heated at 90° C. for 16 hours. The reaction was diluted with sodium hydrogen carbonate (sat, 30 ml) and extracted with ethyl acetate (2×20 ml). The extracts were washed with water (×3) and brine, dried (MgSO₄) and evaporated in vacuo to a dark oil, which was purified by flash column chromatography on silica eluting with DCM: MeOH:NH₃(aq) (120:8:1) to give a brown gum. The gum was further purified flash column chromatography on silica eluting with EtOAc in isohexane (50%+1% NH₃(aq)) to give the desired compound as a clear foam (241 mg, 72%). δ (¹H, 400 MHz, CDCl₃) 1.28-1.32 (2H, m), 1.45-1.71(8H, m), 2.38-2.44 (4H, m), 2.60-2.70 (4H, m), 3.16 (2H, dd, J=16.0 & 10.1 Hz), 3.42 (2H, s), 3.67 (2H, q, J=8.6 Hz), 3.79 (2H, s), 7.00 (1 H, d, J=7.8 Hz), 7.13-7.16 (2H, m), and 7.22-7.32 (4 H, m). (ES+) 560 ([MH]⁺).

Step 4

A solution of the alkyne from Step 3 (115 mg, 0.21 mmol), benzoic acid (1.0 M in dioxane, 20 µl, 0.02 mmol) and tetrakis-triphenylphospine palladium(0) (13 mg, 0.01 mmol) in dioxane (4.0 ml) was degassed and heated at reflux for 48 hours. The reaction was purified by SCX ion exchange resin eluting with ammonia (2M in methanol) to give after evaporation a dark gum. The gum was further purified by flash column chromatography on silica eluting with EtOAc:isohexane (1:1) to give a pale yellow foam (41 mg, 36%). δ (¹H, 400 MHz, CDCl₃) 1.25-1.48 (3H, m), 1.48-1.76 (7H, m), 1.88-2.08 (1H, m), 2.42-2.44 (2H, m), 2.67 (2H, dd, J=16.0 & 7.7 Hz), 2.80-2.87 (2H, m), 3.10 (2H, dd, J=13.5 & 4.7 Hz), 3.17 (2H, dd, J=16.0 & 7.0 Hz), 3.42 (2H, s), 3.64-3.70 (2H, m), 4.08 (1H, d, J=13.6 Hz), 4.66 (1H, Brs), 6.20-6.27 (1H, m), 6.47 (1H, d, J=16.0 Hz), 7.00 (1 H, d, J=8.8 Hz),7.04 (1H, s), 7.07-7.15 (1H, m), 7.19-7.23 (1H, s) and 7.28-7.33 (4H, m). (ES+) 560 ([MH]⁺).

Example 10

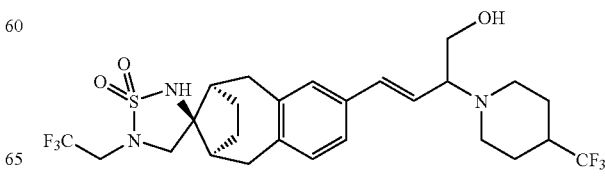

Step 1

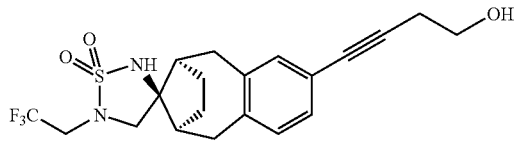

A mixture of Intermediate 1 (100 mg, 0.2 mmol), 3-butyn-1-ol (61 μl, 0.8 mmol), tetrakis-triphenylphospine palladium (0) (12 mg, 5 mol %), triphenylphosphine (5.2 mg, 10 mol %) and copper iodide (4 mg, 10 mol %) in triethylamine (3 ml) was purged with nitrogen and then heated at 100° C. for 16 hours. Dioxane (3 ml), tetrakis-triphenylphospine palladium(0) (12 mg, 5 mol %), triphenyl phosphine (5.2 mg, 10 mol %) and copper iodide (4 mg, 10 mol %) were added and the reaction was heated at 100° C. for 48 hours. The reaction was diluted with sodium hydrogen carbonate (sat, 20 ml) and extracted with ethyl acetate (2×25 ml). The extracts were washed with water (×3) and brine, dried ($MgSO_4$) and evaporated in vacuo to a brown gum, which was purified by flash column chromatography on silica eluting with EtOAc:isohexane (2:3) to give a white solid (30 mg, 35%). δ ($^1$H, 400 MHz, $CDCl_3$) 1.25-1.34 (2H, m), 1.68-1.72 (2H, m), 1.77 (1H, t, J=6.2 Hz), 2.43 (2H, t, J=7.2 Hz), 2.61-2.71(4H, m), 3.17 (2H, dd, J=16.0 & 7.4 Hz), 3.42 (2H, s), 3.67 (2H, q, J=8.7 Hz), 3.81 (2H, q, J=6.2 Hz), 4.66 (1H, brs), 7.02 (1 H, d, J=8.2 Hz), and 7.17-7.18 (2H, m).

Step 2

A solution of the product of Step 1 (24 mg, 0.06 mmol), 4-trifluoromethyl piperidine (9 mg, 0.05 mmol), benzoic acid (0.1M in dioxane, 60 μl, 0.0066 mmol) and tetrakis-triphenylphospine palladium(0) (4 mg, 5 mol %) in dioxane (0.4 ml) was degassed and heated at reflux for 65 hours. The reaction was purified by SCX ion exchange resin eluting with ammonia (2M in methanol) to give after evaporation a pale gum. The gum was further purified by preparative TLC eluting with ethyl acetate to give a pale gum (5 mg, 15%). ($^1$H, 360 MHz, $CDCl_3$) 1.25-1.41 (2H, m), 1.53-2.04 (7H, m), 2.13-2.19 (2H, m), 2.44-2.55 (3H, m), 2.65-2.72 (3H, m) 2.87-2.91 (1H, m), 3.05 (1H, d, J=11.2 Hz), 3.16-3.32 (3H, m), 3.43 (2H, s), 3.55-3.71 (4H, m), 4.72 (1H, brs), 6.08 (1H, dd, J=16.0 & 8.9 Hz), 6.48 (1H, d, J=16.0 Hz) and 7.04-7.15 (3 H, m). (ES+) 582 ([MH]$^+$).

Example 11

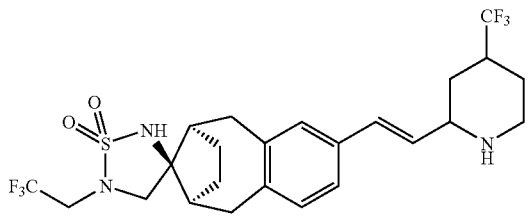

Step 1.

A solution of Intermediate 1 (0.508 g), bis (pinacolato) diboron (0.279 g), Pd(dppf)$Cl_2$.DCM (82 mg), dppf (55 mg) and potassium acetate (0.294 g) in dry degassed DMF (7 ml) was heated at 100° C. under nitrogen for 3 hours. The reaction was allowed to cool and poured into water (35 ml) and extracted with EtOAc (3×20 ml). The combined organic phases were washed with water (30 ml) then brine (50 ml). Drying, concentration and column chromatography on silica eluting with 15-20% EtOAc/hexane gave the boronate ester (0.375 g, 77%).

Step 2.

Triethylamine (8.0 ml), 4-trifluoromethylpiperidine (8.00 g) and $BOC_2O$ (12.5 g) in THF (100 ml) was stirred for 16 hours at rt. Added water (60 ml) and extracted with EtOAc (3×50 ml). The combined organic phases were washed with brine (50 ml). Drying, concentration and column chromatography on silica eluting with 5% EtOAc/hexane gave the BOC-protected amine (12.51 g, 95%).

Step 3.

Sec-butyllithium (7 ml, 1.3M in cyclohexane) was added to a solution of the product from Step 2 (2.00 g) and TMEDA (1.2 ml) in dry ether (15 mL) at −78° C. under nitrogen. The reaction was stirred at −20° C. for 30 mins then cooled to −78° C. Dimethylformamide (0.9 ml) in dry ether (2 ml) was added and the reaction was stirred at −78° C. for 45 mins. The reaction was quenched with saturated ammonium chloride solution (20 ml) and extracted with EtOAc (3×20 ml). The combined organic phases were washed with brine (20 ml). Drying, concentration and column chromatography on silica eluting with 10% EtOAc/hexane gave the 2-formyl derivative of the BOC-protected amine (2.083 g, 94%).

Step 4.

A solution of the aldehyde from Step 3 (0.337 g) and iodoform (0.943 g) in dry THF (10 ml) was added dropwise to chromium II chloride (0.884 g) in dry THF (10 ml). The reaction was stirred in the dark for 16 hours at rt then saturated ammonium chloride solution (20 ml) was added. The mixture was extracted with EtOAc (3×30 ml). The combined organic phases were washed with water (20 ml). Drying, concentration and column chromatography on silica eluting with 5% ether/hexane gave the 2-(2-iodoethenyl) derivative of the BOC-protected amine (0.126 g, 26%).

Step 5.

A solution of the boronate from Step 1 (0.166 g), the vinyl iodide from Step 4 (0.126 g), $Pd_2dba_3$ (7 mg), tributylphosphine (93 μl, 0.2M in dioxan) and cesium carbonate (0.304 g) in degassed aqueous THF (3 ml) was heated at 60° C. in a sealed tube for 16 hours. The reaction was allowed to cool, added water (10 ml) and extracted with EtOAc (3×10 ml). The combined organic phases were washed with brine (20 ml). Drying, concentration and column chromatography on silica eluting with 10-20% EtOAc/hexane gave the Boc-protected product (0.150 g, 75%). The product was dissolved in $Et_2O$, cooled to 0° C. and bubbled in HCl for 5 mins. Concentration and trituration with $Et_2O$ gave the title compound as the HCl salt. $^1$H NMR (360 MHz, MeOH) $δ_H$ 1.19 (2H, m), 1.75 (2H, m), 1.93 (1H, m), 2.17 (3H, m), 2.45 (2H, m), 2.65 (2H, m), 2.95 (1H, m), 3.31 (5H, m), 3.49 (2H, s), 3.86 (2H, q, J=9.2), 4.36 (2H, m), 6.43 (1H, dd, J=15.6, 7.9), 6.85 (1H, d, J=15.6), 7.11 (1H, d, J=7.9), 7.27 (2H, m). MS(ES+) 538, MH$^+$.

The invention claimed is:

1. A compound of formula I:

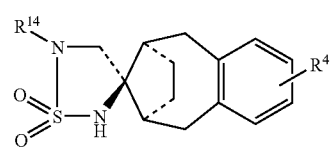

(I)

wherein R$^4$ is selected from:

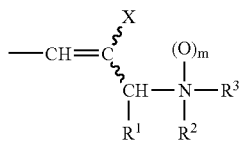

X represents H, halogen, CN or methyl;

$R^1$ represents H or $C_{1-4}$alkyl which is optionally substituted with OH or $C_{1-4}$alkoxy;

$R^2$ and $R^3$ together with the nitrogen to which they are mutually attached complete a monocyclic heterocyclic ring system of 5-10 ring atoms selected from C, N, O and S, said ring system optionally having an additional benzene or heteroaryl ring fused thereto, said heterocyclic system and optional fused ring bearing 0-3 substituents independently selected from halogen, oxo, $NO_2$, CN, $R^{12}$, Ar, $ArCH_2O$, ArO, $ArOCH_2$, $-OR^{11}$, $-SR^{11}$, $-SO_2R^{12}$, $-COR^{11}$, $-CO_2R^{11}$, $-CON(R^{11})_2$, $-OCOR^{12}$, $-N(R^{11})_2$ and $-NR^{11}COR^{12}$;

and when $R^1$ completes a ring with $R^2$, $R^3$ represents H, $C_{1-6}$alkyl, $C_{2-6}$acyl, $C_{2-6}$alkenyl or benzyl;

m is 0 or 1, with the proviso that when m is 1 neither $R^2$ nor $R^3$ is H and $R^3$ is not acyl, and that m is 1 when X and $R^1$ are both H;

$R^{11}$ represents H or $R^{12}$;

$R^{12}$ represents $C_{1-6}$alkyl which optionally bears up to 3 halogen substituents or one substituent selected from CN, OH, $C_{1-4}$alkoxy and $C_{1-4}$alkoxycarbonyl;

$R^{14}$ represents H or $C_{1-6}$alkyl, $C_{3-7}$cycloalkyl, $C_{3-6}$cycloalkyl$C_{1-6}$alkyl, $C_{2-6}$alkenyl, $C_{2-6}$alkynyl, phenyl or benzyl, any of which optionally bear up to 3 halogen substituents or one substituent selected from CN, $NO_2$, OH, $C_{1-4}$alkoxy, $CO_2H$, $C_{1-4}$alkoxycarbonyl, $C_{2-6}$acyl, $C_{2-6}$acyloxy amino, $C_{1-4}$alkylamino, di($C_{1-4}$alkyl)amino, $C_{2-6}$acylamino, carbamoyl, $C_{1-4}$alkylcarbamoyl and di($C_{1-4}$alkyl)carbamoyl; and Ar represents phenyl or heteroaryl either of which optionally bears up to 3 substituents independently selected from halogen, $CF_3$, $NO_2$, CN, $OCF_3$, $C_{1-6}$alkyl and $C_{1-6}$alkoxy; or a pharmaceutically acceptable salt thereof.

2. A compound according to claim 1 of formula II:

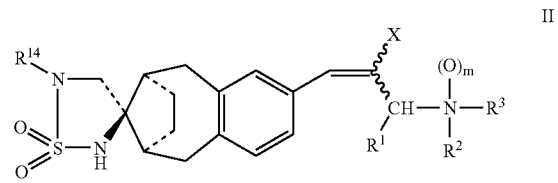

or a pharmaceutically acceptable salt thereof.

3. A compound according to claim 1 wherein $R^{14}$ is 2,2,2-trifluoroethyl, X is F, CN or methyl, and $R^1$ is H.

4. A compound according to claim 1 wherein m is 1 and X and $R^1$ are both H.

5. A pharmaceutical composition comprising a compound according to claim 1 and a pharmaceutical carrier.

6. A method of treatment of Alzheimer's disease comprising administering to that subject an effective amount of a compound according to claim 1.

* * * * *